United States Patent
Lenz

(10) Patent No.: US 8,435,752 B2
(45) Date of Patent: May 7, 2013

(54) GENE POLYMORPHISMS PREDICTIVE FOR DUAL TKI THERAPY

(75) Inventor: Heinz-Josef Lenz, Los Angeles, CA (US)

(73) Assignee: University of Southern California, Los Angeles, CA (US)

(*) Notice: Subject to any disclaimer, the term of this patent is extended or adjusted under 35 U.S.C. 154(b) by 610 days.

(21) Appl. No.: 12/523,514

(22) PCT Filed: Jan. 17, 2008

(86) PCT No.: PCT/US2008/000661
§ 371 (c)(1),
(2), (4) Date: Feb. 24, 2010

(87) PCT Pub. No.: WO2008/088861
PCT Pub. Date: Jul. 24, 2008

(65) Prior Publication Data
US 2010/0183593 A1  Jul. 22, 2010

Related U.S. Application Data

(60) Provisional application No. 60/885,620, filed on Jan. 18, 2007.

(51) Int. Cl.
*G01N 33/574* (2006.01)

(52) U.S. Cl.
USPC .................................. 435/7.23; 435/6.14

(58) Field of Classification Search .......... None
See application file for complete search history.

(56) References Cited

U.S. PATENT DOCUMENTS

| | | | |
|---|---|---|---|
| 4,656,127 A | 4/1987 | Mundy | |
| 4,683,195 A | 7/1987 | Mullis et al. | |
| 4,683,202 A | 7/1987 | Mullis | |
| 4,704,692 A | 11/1987 | Ladner | |
| 4,816,567 A | 3/1989 | Cabilly et al. | |
| 4,873,316 A | 10/1989 | Meade et al. | |
| 4,998,617 A | 3/1991 | Ladd, Jr. et al. | |
| 5,176,996 A | 1/1993 | Hogan et al. | |
| 5,210,015 A | 5/1993 | Gelfand et al. | |
| 5,225,539 A | 7/1993 | Winter | |
| 5,256,775 A | 10/1993 | Froehler | |
| 5,264,564 A | 11/1993 | Matteucci | |
| 5,304,489 A | 4/1994 | Rosen | |
| 5,530,101 A | 6/1996 | Queen et al. | |
| 5,547,835 A | 8/1996 | Köster | |
| 5,565,362 A | 10/1996 | Rosen | |
| 5,571,676 A | 11/1996 | Shuber | |
| 5,580,732 A | 12/1996 | Grossman et al. | |
| 5,585,089 A | 12/1996 | Queen et al. | |
| 5,605,798 A | 2/1997 | Köster | |
| 5,627,052 A | 5/1997 | Schrader | |
| 5,693,762 A | 12/1997 | Queen et al. | |
| 5,714,352 A | 2/1998 | Jakobovits | |
| 5,723,323 A | 3/1998 | Kauffman et al. | |
| 5,763,192 A | 6/1998 | Kauffman et al. | |
| 5,766,886 A | 6/1998 | Studnicka et al. | |
| 5,814,476 A | 9/1998 | Kauffman et al. | |
| 5,817,483 A | 10/1998 | Kauffman et al. | |
| 5,824,514 A | 10/1998 | Kauffman et al. | |
| 5,827,690 A | 10/1998 | Meade et al. | |
| 5,849,992 A | 12/1998 | Meade et al. | |
| 5,858,659 A | 1/1999 | Sapolsky et al. | |
| 5,952,172 A | 9/1999 | Meade et al. | |
| 5,968,740 A | 10/1999 | Fodor et al. | |
| 5,976,862 A | 11/1999 | Kauffman et al. | |
| 5,994,616 A | 11/1999 | Rosen | |
| 6,018,041 A | 1/2000 | Drmanac et al. | |
| 6,025,136 A | 2/2000 | Drmanac | |
| 6,075,181 A | 6/2000 | Kucherlapati et al. | |
| 6,180,370 B1 | 1/2001 | Queen et al. | |
| 6,204,023 B1 | 3/2001 | Robinson et al. | |
| 6,455,249 B1 | 9/2002 | Hsu et al. | |
| 6,602,684 B1 | 8/2003 | Umaña et al. | |
| 6,632,926 B1 | 10/2003 | Chen et al. | |
| 6,716,581 B2 | 4/2004 | Lenz et al. | |
| 7,862,995 B2* | 1/2011 | Bacus et al. ................. | 435/6.14 |
| 2004/0067519 A1 | 4/2004 | Lenz et al. | |
| 2006/0094012 A1 | 5/2006 | Lenz et al. | |
| 2006/0094068 A1 | 5/2006 | Bacus et al. | |
| 2006/0115827 A1 | 6/2006 | Lenz | |
| 2006/0160074 A1 | 7/2006 | Dorn et al. | |
| 2007/0207486 A1 | 9/2007 | Lenz | |
| 2007/0218487 A1 | 9/2007 | Lenz | |
| 2007/0244083 A1 | 10/2007 | Lenz | |
| 2008/0286789 A1 | 11/2008 | Lenz et al. | |
| 2009/0181016 A1 | 7/2009 | Lenz | |

FOREIGN PATENT DOCUMENTS

| | | |
|---|---|---|
| WO | WO 2004/011625 A2 | 2/2004 |
| WO | WO 2005/017493 A2 | 2/2005 |
| WO | WO 2005/120512 A2 | 12/2005 |
| WO | WO 2005/121380 A1 | 12/2005 |
| WO | WO 2008/088893 A2 | 12/2005 |
| WO | WO 2006/012361 A2 | 2/2006 |
| WO | WO 2006/061253 A2 | 6/2006 |
| WO | WO 2007/103814 A2 | 9/2007 |
| WO | WO 2007/103814 A2 | 9/2007 |
| WO | WO 2007/103823 A2 | 9/2007 |

(Continued)

OTHER PUBLICATIONS

Hirshhorn et al., Genetics in Medicine, 2002, 4(2): 45-61.*

(Continued)

*Primary Examiner* — Mark Halvorson

(74) *Attorney, Agent, or Firm* — Foley & Lardner LLP; Antoinette F. Konski; Alex Y. Nie

(57) ABSTRACT

The invention provides compositions and methods for determining the likelihood of successful treatment with dual therapy such as lapatinib. The methods comprise determining the genomic polymorphism or expression level of a gene present in a predetermined region of a gene of interest and correlating the polymorphism or expression level to the predictive response. Patients identified as likely responsive are then treated with the appropriate therapy.

6 Claims, No Drawings

FOREIGN PATENT DOCUMENTS

| | | |
|---|---|---|
| WO | WO 2008/088854 A2 | 7/2008 |
| WO | WO 2008/088855 A2 | 7/2008 |
| WO | WO 2008/088860 A2 | 7/2008 |
| WO | WO 2008/088861 A2 | 7/2008 |
| WO | WO 2008/089465 A2 | 7/2008 |
| WO | WO 2009/140556 A2 | 11/2009 |
| WO | WO 2010/124264 A2 | 10/2010 |
| WO | WO 2010/124265 A1 | 10/2010 |

OTHER PUBLICATIONS

Erichsen et al. Br J. Cancer, 2004, vol. 90, pp. 747-751.*
Lenz (J Clin Oncol, 2004, 22:2519-2521.*
Spector et al, J Clin Oncol, 2005, 23:2502-2512.*
Zhang, W. et al. (2005) "Genomic Polymorphisms of Angiogenesis Pathway Predict Radiosensitivity in Rectal Cancer," Int. J. Radiation Oncology, Biology, Physics 63(2), 2091:S284.
Lenz, H-J. et al. (2006) "EGFR-Targeted Therapies in Solid Tumors," Retrieved from the internet from: URL: http://www.CancerPublications.com.
Pander, J. et al. (2007) "Pharmacogenetics of EGFR and VEGF inhibition," Drug Discovery Today 12(23/24):1054-1060.
Vallbohmer, D. et al. (2005) "Molecular Determinants of Cetuximab Efficacy," J. Clin. Oncol. 23(15):3536-3544.
Kuniyasu, H. et al. (2000) "Induction of Angiogenesis by Hyperplastic Colonic Mucosa Adjacent to Colon Cancer," American Journal of Pathology 157(5):1523-1535.
Liotta, L.A. et al. (2001) "The microenvironment of the tumour—host interface," Nature 411:375-379.
Loktionov, A. (2004) "Common gene polymorphisms, cancer progression and prognosis," Cancer Letters 208:1-33.
Shaye, O.S. et al. (2007) "Polymorphisms in angiogenesis related genes predict clinical outcome in patients (pts) with metastatic colorectal cancer (mCRC) treated with first line 5-FU or capecitabine in combination with oxaliplatin and bevacizumab (FOLFOX/BV or XELOX/BV)," Journal of Clinical Oncology, 2007 ASCO Annual Meeting Proceedings 25(18S):10576.
Allen, W.L. et al. (2006) "Predicting the outcome of chemotherapy for colorectal cancer," Current Opinion in Pharmacology 6:332-336.
Konecny, G.E. et al. (2006) "Activity of the Dual Kinase Inhibitor Lapatinib (GW572016) against HER-2-Overexpressing and Trastuzumab-Treated Breast Cancer Cells," Cancer Res 66(3):1630-1639.
Burris, H.A., III (2004) "Dual Kinase Inhibition in the Treatment of Breast Cancer: Initial Experience with the EGFR/ErbB-2 Inhibitor Lapatinib," The Oncologist 9(3):10-15.
Zhang, W. et al. (2005) "Cyclin D1 and epidermal growth factor polymorphisms associated with survival in patients with advanced colorectal cancer treated with Cetuximab," Pharmacogenetics and Genomics 16:475-483.
Zhang, W. et al. (2005) "Gene Polymorphisme of Epidermal Growth Factor Receptor and its Downstream Effector, Interleukin-8, Predict Oxaliplatin Efficacy in Patients with Advanced Colorectal Cancer," Clinical Colorectal Cancer 5(2):124-131.
Eroglu, A. et al. (2006) "Vascular endothelial growth factor 936 C/T polymorphism in cancer patients," Annals of Oncology 17:1467-1468.
Kataoka, N. et al. (2006) "Population-Based Case-Control Study of VEGF Gene Polymorphisms and Breast Cancer Risk among Chinese Women," Cancer Epidemiology, Biomarkers & Prevention 15(6):1148-1152.
Geyer, C.E. et al. (2006) "Lapatinib plus Capecitabien for HER2-Positive Advanced Breast Cancer," The New England Journal of Medicine 355(26):2733-2743.
Burris, H.A., III (2005) "Phase I Safety, Pharmacokinetics, and Clinical Activity Study of Lapatinib (GW572016), a Reversible Dual Inhibitor of Epidermal Growth Factor Receptor Tyrosine Kinases, in Heavily Pretreated Patients with Metastatic Carcinomas," J. Clin. Oncol. 23(23):5305-5313.
Manegold, P.C. et al. (2008) "ICAM-1, GRP-78, and NFkB gene polymorphisms and clinical outcome in patients (pts) with metastatic colorectal cancer (mCRC) treated with first line 5-FU or capecitabine in combination with oxaliplatin and bevacizumab (FOLFOX/BV or XELOX/BV)," Journal of Clinical Oncology, 2008 ASCO Annual Meetin Proceedings 26(15S):4134.
Smith, K.C. et al. (2004) "Cytokine gene polymorphisms and breast cancer susceptibility and prognosis," European Journal of Immunogenetics 31:167-173.
Ning, Y. et al. (2009) "VEGF and VEGFR1 gene expression levels and tumor recurrence in adjuvant colon cancer," ASCO Annual Meeting 2009, Abstract No. 4040.
Vallbohmer, D. et al. (2006) "Molecular determinants of irinotecan efficacy," Int. J. Cancer 119:2435-2442.
Lurje, G. et al. (2008) "Polymorphisms in VEGF and IL-8 predict tumor recurrence in stage III colon cancer," Annals of Oncology 19:1734-1741.
Zhang, W. et al. (2009) "Genetic variants in angiogenesis pathway associated with clinical outcome in NSCLC patients (pts) treated with bevacizumab in combination with carboplatin and paclitaxel: Subset pharmacogenetic analysis of ECOG 4599," ASCO Annual Meeting 2009, Abstract No. 8032.
Lurje, G. et al. (2010) "Genetic variations in angiogenesis pathway genes associated with clinical outcome in localized gastric adenocarcinoma," Annals of Oncology 21(1):78-86.
Yan, L. et al. (2005) "Pharmacogenetics and pharmacogenomics in oncology therapeutic antibody development," BioTechniques 39:565-568.
Renzoni, E. et al. (2000) "Distribution of Novel Polymorphisms of the Interleukin-8 and CXC Receptor 1 and 2 Genes in Systemic Sclerosis and Cryptogenic Fibrosing Alveolitis," Arthritis & Rheumatism 43(7):1633-1640.
Lurje, G. et al. (2008) "Polymorphisms in *Cyclooxygenase*-2 and *Epidermal Growth Factor Receptor* Are Associated with Progression-Free Survival Independent of K-ras in Metastatic Colorectal Cancer Patients Treated with Single-Agent Cetuximab," Clin. Cancer Res. 14(23):7884-7895.
Gold, P.J. et al. (2010) "Cetuximab as second-line therapy in patients with metastatic esophageal adenocarcinoma: A phase II Southwest Oncology Group Study (S0415)," J Thorac Oncol. 5(9):1472-1476.
Azuma, M. et al. 2007 ASCO Annual Meeting Proceedings, Part I, J. Clinical Oncology 25(18S) Jun. 20 Supp):Abstract No. 4113.
Balasubramanian, S.P. et al. (2002) "Role of genetic polymorphisms in tumour angiogenesis," British Journal of Cancer 87:1057-1065.
Ban, N. et al. (1996) "Transfection of Glutathione S-Transferase (GST)-pi Antisense Complementary DNA Increases the Sensitivity of a Colon Cancer Cell Line to Adriamycin, Cisplatin, Melphalan, and Etoposide," Cancer Research 56(15):3577-3582.
Bello, C.L. et al. 2006 ASCO Annual Meeting Proceedings, J. Clinical Oncology 24(18S) Jun. 20 Supp):Abstract No. 4045.
Chang, H. et al. 2007 ASCO Annual Meeting Proceedings, Part I, J. Clinical Oncology 25(18S) (Jun. 20 Supp):Abstract No. 4647.
du Manoir, J.M. et al. (2006) "Strategies for Delaying or Treating in vivo Acquired Resistance to Trastuzumab in Human Breast Cancer Xenografts," Clin Cancer Res 12(3):904-916.
Eberhart, C.E. et al. (1994) "Up-regulation of Cyclooxygenase 2 Gene Expression in Human Colorectal Adenomas and Adenocarcinomas," Gastroenterology 107:1183-1188.
Edelman, G.M. (1988) "Morphoregulatory Molecules," Biochemistry 27(10):3533-3543.
Evans, W.E. et al. (1999) "Pharmacogenomics: Translating Functional Genomics into Rational Therapeutics," Science 286:487-491.
Folkman, J. (2002) "Role of Angiogenesis in Tumor Growth and Metastasis," Semin Oncol 29(Suppl 16):15-18.
Fox, S.H. et al. (1998) "Angiogenesis in Normal Tissue Adjacent to Colon Cancer," Journal of Surgical Oncology 69:230-234.
Gorski, D.H. et al. (1999) "Blockade of the Vascular Endothelial Growth Factor Stress Response Increases the Antitumor Effects of Ionizing Radiation," Cancer Research 59:3374-3378.
Goto, S. et al. (1999) "Overexpression of Glutathione S-Transferase pi Enhances the Adduct Formation of Cisplatin with Glutathione in Human Cancer Cells," Free Rad Res 31(6):549-558.
Iqbal, S. et al. (2003) "Targeted Therapy and Pharmacogenomic Programs," Cancer Supplement 97(8):2076-2082.

Ishimitsu, T. et al. (2003) "Variations of Human Adrenomedullin Gene and Its Relation to Cardiovascular Diseases," Hypertens Res 25(Suppl):S129-S134.

Jin, Q. et al. (2005) "Vascular Endothelial Growth Factor Polymorphisms in Relation to Breast Cancer Development and Prognosis," Clin Cancer Res 11(10):3647-3653.

Kastan, M.B. et al. (1991) "Participation of p53 Protein in the Cellular Response to DNA Damage," Cancer Research 51:6304-6311.

Kuniyasu, H. et al. (2000) "Induction of Angiogenesis by Hyperplastic Colonic Mucosa Adjacent to Colon Cancer," Am J Pathol 157(5):1523-1535.

Ladner, R.D. et al. 2007 ASCO Annual Meeting Proceedings, Part I, J. Clinical Oncology 25(18S) (Jun. 20 Supp):Abstract No. 4130.

Lenz, H. et al. 2007 ASCO, 2007 Gastrointestinal Cancers Symposium:Abstract No. 401.

Lenz, H-J. (2006) "Pharmacogenomics and Colorectal Cancer", Advances in Experimental Medicine and Biology 587:211-231.

Levine, A.J. (1992) "The p53 tumor-suppressor gene," The New England Journal of Medicine 326(20):1350-1352.

Levine, A.M. et al. 2004 ASCO Annual Meeting Proceedings, J. Clinical Oncology 22(14S) (Jul. 15 Supp):Abstract No. 3008.

Mallik, N. et al. 2004 ASCO Annual Meeting Proceedings, J. Clinical Oncology 22(14S) (Jul. 15 Supp):Abstract No. 3606.

Mauceri, H.J. et al. (1996) "Tumor Necrosis Factor alpha (TNF-alpha) Gene Therapy Targeted by Ionizing Radiation Selectively Damages Tumor Vasculature," Cancer Research 56:4311-4314.

Mauceri, H.J. et al. (1998) "Combined effects of angiostatin and ionizing radiation in antitumour therapy," Nature 394:287-291.

Maurer, C.A. et al. (1998) "Over-expression of ICAM-1, VCAM-1 and ELAM-1 might influence tumor progression in colorectal cancer," Int. J. Cancer (Pred. Oncol.) 79:76-81.

Mauritz, R. et al. (2006) "Pharmacogenetics of Colon Cancer and Potential Implications for 5-Fluorouracil-Based Chemotherapy," Current Pharmacogenomics 4:57-67.

Miller, K.D. et al. (2005) "Randomized Phase III Trial of Capecitabine Compared With Bevacizumab Plus Capecitabine in Patients With Previously Treated Metastatic Breast Cancer," J Clin Oncol 23(4):792-799.

Notice of Allowance for U.S. Appl. No. 11/681,695, dated Apr. 14, 2010.

Notice of Allowance for U.S. Appl. No. 12/523,521, dated Feb. 28, 2012.

Nunez, M.I. et al. (1996) "Relationship between DNA damage, rejoining and cell killing by radiation in mammalian cells," Radiotherapy and Oncology 39:155-165.

Office Action for U.S. Appl. No. 11/681,695, dated Jul. 22, 2009.

Office Action for U.S. Appl. No. 12/523,521, dated Aug. 16, 2011.

Office Action for U.S. Appl. No. 12/600,458, dated Aug. 21, 2012.

Park, D.J. et al. (2006) "Determinants of chemosensitivity in gastric cancer," Curr. Opin. Pharma. 6(4):337-344.

Pasqualetti, G. et al. (2007) "Vascular endothelial growth factor pharmacogenetics: a new perspective for anti-angiogenic therapy," Pharmacogenomics 8(1):49-66.

Renner, W. (2000) "A Common 936 C/T Mutation in the Gene for Vascular Endothelial Growth Factor Is Associated with Vascular Endothelial Growth Factor Plasma Levels," J. Vascular Res. 37:443-448.

Rhodes, K.E. et al. 2005 ASCO Annual Meeting Proceedings, Part I of II, J. Clinical Oncology 23(16S) (Jun. 15 Supp):Abstract No. 3606.

Ruoslahti, E. et al. (1988) "Fibronectin and Its Receptors," Ann. Rev. Biochem. 57:375-413.

Schultheis, A.M. et al. 2006 ASCO Annual Meeting Proceedings, Part I, J. Clinical Oncology 24(18S) (Jun. 20 Supp):Abstract No. 5017.

Schultheis, A.M. et al. (2008) "Polymorphisms and Clinical Outcome in Recurrent Ovarian Cancer Treated with Cyclophosphamide and Bevacizumab," Clin Cancer Res 14(22):7554-7563.

Stoehlmacher, J. et al. (2002) "Association Between Glutathione S-Transferase P1, T1, and M1 Genetic Polymorphism and Survival of Patients With Metastatic Colorectal Cancer," J Natl Cancer Inst 94:936-942.

Stoeltzing, O. et al. (2003) "New Approaches to the Treatment of Hepatic Malignancies: Angiogenesis and Antiangiogenic Therapy of Colon Cancer Liver Metasis," Annals of Surgical Oncology 10(7):722-733.

Wachsberger, P. et al. (2003) "Tumor Response to Ionizing Radiation Combined with Antiangiogenic or Vascular Targeting Agents: Exploring Mechanisms of Interaction," Clin Cancer Res 9:1957-1971.

Yanagisawa, T. et al. (1998) "Increased expression of human DNA repair genes, XRCC1, XRCC3 and RAD51, in radioresistant human KB carcinoma cell line N10," Oral Oncology 34:524-528.

Yang, D. et al. 2004 ASCO Annual Meeting Proceedings, Post-Meeting Edition, J. Clinical Oncology 22(14S) (Jul. 15 Supp):Abstract No. 9526.

Yuan, A. et al. (2000) "Interleukin-8 Messenger Ribonucleic Acid Expression Correlates with Tumor Progression, Tumor Angiogenesis, Patient Survival, and Timing of Relapse in Non-Small-Cell Lung Cancer," Am J Respir Crit Care Med 162:1957-1963.

Yun, J. et al. 2003 ASCO Annual Meeting, Proc Am Soc Clin Oncol 22:Abstract No. 847.

Zhang, W. et al. (2003) "Interleukin-8 (IL-8) Promoter Region Gene Polymorphism Predicts Pelvic Recurrence after Chemo-radiation in Patients with Rectal Cancer," J. Radiation Oncology 57(2):S382.

Zhang, W. et al. (2005) "Association Between Dinucleotide Repeat(CA) Polymorphism of Nuclear Factor Kappa-Bata(NF-KB) and Local Recurrence of Stage II/III Rectal Cancer Patients Treated with Chemoradiation," Proceedings of the 46th Annual ASTRO Meeting, 2148:S423.

Zhang, W. et al. 2007 ASCO Annual Meeting Proceedings, Part I, J. Clinical Oncology 25(18S) (Jun. 20 Supp):Abstract No. 4128.

* cited by examiner

GENE POLYMORPHISMS PREDICTIVE FOR DUAL TKI THERAPY

CROSS-REFERENCE TO RELATED APPLICATION

The present application is a national stage application under 35 U.S.C. §371 of International Application No. PCT/US2008/000661, filed Jan. 17, 2008, which in turn claims the benefit under 35 U.S.C. §119(e) of U.S. Provisional Ser. No. 60/885,620, filed Jan. 18, 2007, the contents of which is hereby incorporated by reference in its entirety into the present disclosure.

STATEMENT OF GOVERNMENT SUPPORT

This invention was supported in whole or in part with a grant from the U.S. National Cancer Institute. Accordingly, the U.S. government may have rights to the inventions disclosed herein.

FIELD OF THE INVENTION

This invention relates to the field of pharmacogenomics and specifically to the application of genetic polymorphism(s) to diagnose and treat diseases.

BACKGROUND OF THE INVENTION

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Pharmacogenetics and pharmacogenomics are multidisciplinary research efforts to study the relationship between genotype, gene expression profiles, and phenotype, as expressed in variability between individuals in response to or toxicity from drugs. Indeed, it is now known that cancer chemotherapy is limited by the predisposition of specific populations to drug toxicity or poor drug response. For a review of the use of germline polymorphisms in clinical oncology, see Lenz, H.-J. (2004) J. Clin. Oncol. 22(13):2519-2521; Park, D. J. et al. (2006) Curr. Opin. Pharma. 6(4):337-344; Zhang, W. et al. (2006) Pharma. and Genomics 16(7):475-483 and U.S. Patent Publ. No. 2006/0115827. For a review of pharmacogenetic and pharmacogenomics in therapeutic antibody development for the treatment of cancer, see Yan and Beckman (2005) Biotechniques 39:565-568.

Colorectal cancer (CRC) represents the second leading lethal malignancy in the USA. In 2005, an estimated 145,290 new cases will be diagnosed and 56,290 deaths will occur. Jemal, A. et al. (2005) Cancer J. Clin. 55:10-30. Despite advances in the treatment of colorectal cancer, the five year survival rate for metastatic colon cancer is still low, with a median survival of 18-21 months. Douglass, H. O. et al. (1986) N. Eng. J. Med. 315:1294-1295.

The Food and Drug Administration has approved the use of Cetuximab, an antibody to the epidermal growth factor receptor (EGFR), either alone or in combination with irinotecan (also known as CPT-11 or Camptosar®) to treat patients with EGFR-expressing, metastatic CRC, who are either refractory or intolerant to irinotecan-based chemotherapy. One recent study (Zhang, W. et al. (2006) Pharmocogenetics and Genomics 16:475-483) investigated whether polymorphisms in genes of the EGFR signaling pathway are associated with clinical outcome in CRC patients treated with single-agent Cetuximab. The study reported that the cyclin D1 (CCND1) A870G and the EGF A61G polymorphisms may be useful molecular markers for predicting clinical outcome in CRC patients treated with Cetuximab.

Other polymorphisms have been reported to associated with clinical outcome. Twenty-one (21) polymorphisms in 18 genes involved in the critical pathways of cancer progression (i.e., drug metabolism, tumor microenvironment, cell cycle regulation, and DNA repair) were investigated to determine if they will predict the risk of tumor recurrence in rectal cancer patients treated with chemoradiation. Gordon, M. A. et al. (2006) Pharmacogenomics 7(1):67-88. However, to the best of Applicant's knowledge, correlation of the polymorphisms identified herein and responsiveness to lapatinib therapy has not been previously reported.

DESCRIPTION OF THE EMBODIMENTS

This invention provides methods to identify patients likely to respond to a therapy and to select the appropriate therapy for patients suffering from a gastrointestinal cancer or breast cancer, wherein the appropriate therapy comprises administration of an effective amount of dual EGFR and ErbB-2 inhibitor such as lapatinib, or a chemical equivalent of lapatinib or a biological equivalent of lapatinib (one or more collectively referred to as "dual therapy" for convenience). The therapy may be supplemented or combined with other therapies, examples of which include but are not limited to trastuzumab, capecitabine, letrozole, paclitaxel and FOLFIRI (irinotecan, 5-fluorouracil and leucovorin). The method requires detecting the identity of a genetic marker of a predetermined gene selected from the group identified in Table 1, below. Additional polymorphisms can be assayed and used as negative controls. Suitable negative controls are identified in the experimental section and Table 2.

TABLE 1

| Genetic Marker | Predictive Polymorphism | Measured Response |
|---|---|---|
| IL-8 (T251A SNP) | A/A IL-8 T251A SNP | Improved overall survival |
| IL-8 | Low Expression | Improved Overall Survival |
| HER-2 | High Expression | Improved Overall Survival |
| VEGF (C936T SNP) | T/T or T/C VEGG C936T SNP | Improved Response |
| IL-8 (T251A SNP) | A/A or A/T | Improved Response |

Patients having at least one genetic marker identified under the center column of Table 1 are selected for this therapy because Applicant has shown that patients with these genetic markers exhibit better responses to this therapy than other available therapies, wherein the response is any improvement in the condition, whether clinical or sub-clinical, examples of which include, but are not limited to, improved overall survival or improved response. Additional polymorphisms can be assayed and used as negative controls. Suitable negative controls are identified in the experimental section below and Table 2, below.

TABLE 2

Additional Markers Assayed

| Allele | Polymorphism | Measured Response |
| --- | --- | --- |
| EGF | A61G SNP | No correlation |
| EGFR | G497A SNP | No correlation |
| HER2 | A655G SNP | No correlation |
| COX-2 | G765C SNP | No correlation |
| CyclinD1 | A870G SNP | No correlation |

Suitable patients that are screened for the dual therapy include, but are not limited to those suffering from a solid tumor such as gastrointestinal cancer whether it is metastatic gastrointestinal cancer or non-metastatic gastrointestinal cancer, metastatic breast cancer, inflammatory breast cancer or a non-metastatic breast cancer. Types of metastatic and non-metastatic gastrointestinal cancers includes those selected from rectal cancer, colorectal cancer, gastric cancer, lung cancer, non-small cell lung cancer or esophageal cancer. Additional suitable cancer patients include any those who would have been typically treated by lapatinib therapy or a therapy comprising lapatinib, such as HER-2 positive breast cancer patients, head and neck cancer patients, renal cancer and bladder cancer patients. Where appropriate, such cancers can be metastatic or non-metastatic.

To practice these methods, the sample is a patient sample containing the tumor cell, tumor tissue, normal tissue adjacent to said tumor, normal tissue distal to said tumor or peripheral blood lymphocytes. The sample is comprised of cells or tissues.

In one aspect, the method also requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

These methods are not limited by the technique that is used to identify the polymorphism of interest. Suitable methods include but are not limited to the use of hybridization probes, antibodies, primers for PCR analysis, slides, software and gene chips for high throughput analysis. Additional polymorphisms can be assayed and used as negative controls. Suitable negative controls are identified in the experimental section below and Table 2.

After a patient has been identified as positive for one or more of the polymorphisms identified in Table 1, the method may further comprise, or alternatively consist essentially of, or yet further consist of, administering or delivering an effective amount of a dual EGFR and ErbB-2 therapy, e.g., lapatinib, or a chemical equivalent or a biological equivalent thereof, to the patient. These may be administered alone or in combination with another therapy such as administration of trastuzumab, capecitabine, letrozole, paclitaxel and FOLFIRI (irinotecan, 5-fluorouracil and leucovorin). Methods of administration of pharmaceuticals and biologicals are known in the art. In an alternative embodiment, the patient is treated with any pharmaceutical or biologic that is a known HER-1 or HER-2 inhibitor, such as monoclonal antibodies and monoclonal antibody derivatives. Additional examples are discussed infra.

In a further aspect, the invention is a method comprising comparing the genotype of a suitable patient against the identified genotype of Table 1 alone or in combination with Table 2. Suitable patients are identified above and include, but are not limited to those having a gastrointestinal malignant tumor. If a patient has a genotype the genotype identified in Table 1, then lapatinib, a chemical equivalent or a biological equivalent thereof, is administered or delivered to the patient. This invention also provides the step of administration or delivery of the therapy.

In another aspect, the invention is a method for identifying responsiveness to dual EGFR and ErbB-2 inhibitor therapy, by assaying a suitable patient sample from a suitable patient for the polymorphism identified in Table 1 and/or Table 2, above. Suitable patients are those identified above. Patients who are considered positive responders for dual therapy have a genetic marker identified in the center column of Table 1, above. These patients show responsiveness to dual therapy or a chemical equivalent or a biological equivalent thereof, wherein responsiveness is selected from the group of clinical parameters of reduction in tumor load or size, time to tumor progression or overall survival. In another aspect, the patient is suffering from a solid malignant tumor such as a gastrointestinal tumor, e.g., from rectal cancer, colorectal cancer, metastatic colorectal cancer, colon cancer, gastric cancer, lung cancer, non-small cell lung cancer and esophageal cancer. In yet a further aspect the patient is suffering from gastric cancer. In yet a further aspect, the patient is suffering from metastatic gastric cancer. In a separate aspect, the patient is suffering from breast cancer, metastatic breast cancer or inflammatory breast cancer.

To practice this method, the sample is a patient sample containing the tumor cell, tumor tissue, normal tissue adjacent to said tumor, normal tissue distal to said tumor or peripheral blood lymphocytes. These methods are not limited by the technique that is used to identify the polymorphism of interest. Suitable methods include but are not limited to the use of hybridization probes, antibodies, primers for PCR analysis and gene chips and software for high throughput analysis. Additional polymorphisms can be assayed and used as negative controls which include, but are not limited to those identified in Table 2, below.

In one aspect, the method also requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

This invention also provides a kit, software, a support and/or gene chip for patient sampling and performance of the methods of this invention. The kits contain gene chips, probes or primers that can be used to amplify and/or for determining the molecular structure of the polymorphisms identified above. In an alternate embodiment, the kit contains antibodies or other polypeptide binding agents that are useful to identify a polymorphism of Table 2. Instructions for using the materials to carry out the methods are further provided.

Further provided is a panel of markers for identifying patients for a therapy comprising administration of a dual EGFR and ErbB-2 inhibitor, a chemical equivalent or a biological equivalent thereof, the panel comprising a primer or probe that identifies at least one or more genetic markers of Table 1 alone or in combination the genetic markers of Table 2 or other markers. In an alternate embodiment, the kit contains antibodies or other polypeptide binding agents that are useful to identify a polymorphism of Table 1 and/or Table 2. Instructions for using the materials to carry out the invention are further provided alone or in combination with instructions for administration of a therapy as described herein.

The various embodiments are set forth herein.

MODES FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook et al. (1989) MOLECULAR CLONING: A LABORATORY MANUAL, $2^{nd}$ edition; CURRENT PROTOCOLS IN MOLECULAR BIOLOGY (F. M. Ausubel et al. eds. (1987)); the series METHODS IN ENZYMOLOGY (Academic Press, Inc., N.Y.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); ANIMAL CELL CULTURE (R. I. Freshney ed. (1987)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); IMMUNOCHEMICAL METHODS IN CELL AND MOLECULAR BIOLOGY (Mayer and Walker, eds., Academic Press, London (1987)); HANDBOOK OF EXPERIMENTAL IMMUNOLOGY, Volumes I-IV (D. M. Weir and C. C. Blackwell, eds. (1986)); MANIPULATING THE MOUSE EMBRYO (Cold Spring Harbor Laboratory Press, Cold Spring Harbor, N.Y. (1986)).

Definitions

As used herein, certain terms may have the following defined meanings. As used in the specification and claims, the singular form "a," "an" and "the" include singular and plural references unless the context clearly dictates otherwise. For example, the term "a cell" includes a single cell and a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively include only the steps and compositions as stated and those of no significance to the invention (consisting essentially of) or alternatively, intending only the stated methods steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

The term "antigen" is well understood in the art and includes substances which are immunogenic. The EGFR is an example of an antigen.

A "native" or "natural" or "wild-type" antigen is a polypeptide, protein or a fragment which contains an epitope and which has been isolated from a natural biological source. It also can specifically bind to an antigen receptor.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

When an antibody is combined with the therapy or used diagnostically, they can be polyclonal or monoclonal and can be isolated from any suitable biological source, e.g., murine, rat, sheep and canine. Additional sources are identified infra.

In one aspect, the "biological activity" means the ability of the antibody to selectively bind its epitope protein or fragment thereof as measured by ELISA or other suitable methods. Biologically equivalent antibodies, include but are not limited to those antibodies, peptides, antibody fragments, antibody variant, antibody derivative and antibody mimetics that bind to the same epitope as the reference antibody.

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and $C_H$, domains; a F(ab')$^2$ fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "bispecific molecule" is intended to include any agent, e.g., a protein, peptide, or protein or peptide complex, which has two different binding specificities. The term "multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by heavy chain constant region genes.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

"Lapatinib" (Tykerb®) is an oncolytic dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor or alternatively a HER-1 inhibitor or a HER-2 inhibitor. Several TKIs have been found to have effective antitumor activity and have been approved or are in clinical trials. Examples of such include, but are not limited to Zactima (ZD6474), Iressa (gefitinib) and Tarceva (erlotinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SU11248) and leflunomide (SU101).

A biological equivalent of lapatinib is a peptide, antibody or antibody derivative thereof that is a HER-1 inhibitor and/or a HER-2 inhibitor. Examples of such include but are not limited to the humanized antibody trastuzumab and Herceptin.

"Differentially expressed" as applied to a gene, refers to the differential production of the mRNA transcribed from the gene or the protein product encoded by the gene. A differentially expressed gene may be over expressed (high expression) or under expressed (low expression) as compared to the expression level of a normal or control cell, a given patient population or with an internal control. In one aspect, it refers to a differential that is about 1.5 times, or alternatively, about 2.0 times, alternatively, about 2.0 times, alternatively, about 3.0 times, or alternatively, about 5 times, or alternatively, about 10 times, alternatively about 50 times, or yet further alternatively more than about 100 times higher or lower than the expression level detected in a control sample. The term "differentially expressed" also refers to nucleotide sequences in a cell or tissue which are expressed where silent in a control cell or not expressed where expressed in a control cell. In another aspect, expression level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest.

As used herein, the term "gene of interest" intends one or more genes selected from the group identified in Table 1.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "allelic variant of a polymorphic region of the gene of interest" refers to a region of the gene of interest having one of a plurality of nucleotide sequences found in that region of the gene in other individuals.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

When a genetic marker or polymorphism is used as a basis for selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. As would be well understood by one in the art, measurement of the genetic marker or polymorphism in a clinical setting is a clear indication that this parameter was used as a basis for initiating, continuing, adjusting and/or ceasing administration of the treatments described herein.

The term "treating" as used herein is intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7): 1404-1411.

A "complete response" (CR) to a therapy defines patients with evaluable but non-measurable disease, whose tumor and all evidence of disease had disappeared.

A "partial response" (PR) to a therapy defines patients with anything less than complete response were simply categorized as demonstrating partial response.

"Stable disease" (SD) indicates that the patient is stable.

"Non-response" (NR) to a therapy defines patients whose tumor or evidence of disease has remained constant or has progressed.

"Overall Survival" (OS) intends a prolongation in life expectancy as compared to naïve or untreated individuals or patients.

The term "likely to respond" shall mean that the patient is more likely than not to exhibit at least one of the described clinical parameters or treatment responses, identified above, as compared to similarly situated patients.

Descriptive Embodiments

This invention provides a method for identifying patients likely to respond to a therapy or for selecting a therapeutic regimen or determining if a certain therapeutic regimen is more likely to treat a malignant condition such as cancer or is the appropriate chemotherapy for that patient than other available chemotherapies. In general, a therapy is considered to "treat" cancer if it provides one or more of the following treatment outcomes: reduce or delay recurrence of the cancer after the initial therapy; time to tumor progression (TTP), decrease in tumor load or size (tumor response or TR), increase median survival time (OS) or decrease metastases. The method is particularly suited to determining which patients will likely be responsive or experience a positive treatment outcome to lapatinib or administration of an equivalent thereof. These methods are useful to select therapies for highly aggressive cancers such as gastrointestinal cancers.

In one aspect, this invention is to a method for determining whether a human cancer patient suffering from a gastrointestinal cancer or a breast cancer is likely responsive to administration of a dual EGFR and ErbB-2 inhibitor based therapy by screening a suitable cell or tissue sample isolated from said patient for at least one genetic marker of the group IL-8 T251A SNP; IL-8 expression; HER2 expression or VEGF (C936T), wherein for the genetic marker screened, the presence of at least one genetic maker of the group: A/A for IL-8 T251A SNP; low IL-8 expression; T/T or T/C for VEGF C936T SNP or high HER2 expression, indicates the patient is likely responsive to said dual EGFR and ErbB-2 inhibitor based therapy. In one aspect only one of the noted markers are screened. In another aspect, two of the genetic markers are screened. In a further aspect, three genetic markers are screened. In a yet further aspect, all four genetic markers are screened. In a yet further aspect, one or more of the markers identified in Table 2, are screened.

This invention also provides a method for determining whether a human cancer patient suffering from a gastrointestinal cancer or a breast cancer, is likely responsive to administration of a dual EGFR and Erb-B2 inhibitor based therapy by screening a suitable cell or tissue sample isolated from said patient for a genetic marker of the group: IL-8 T251A; VEGF C936T SNP; wherein for the genetic marker screened, the presence of at least one genetic maker of the group: A/A or A/T for IL-8 T251A or T/T or T/C for VEGF C936T SNP, indicates that the patient is likely responsive to said dual EGFR and ErbB-2 inhibitor based therapy. In one aspect, both are screened from the patient sample. In a further aspect, the expression level of the IL-8 and/or HER-2 gene are screened. In one aspect, all five genetic markers are screened.

Suitable patients for these screens include those suffering from metastatic gastrointestinal cancer, non-metastatic gastrointestinal cancer, metastatic breast cancer or non-metastatic breast cancer. In one aspect, the breast cancer is metastatic breast cancer, inflammatory breast cancer or a non-metastatic breast cancer. In another aspect, the cancer is selected from the group of rectal cancer, colon cancer, colorectal cancer, colon cancer, gastric cancer, metastatic gastric cancer, lung cancer, non-small cell lung cancer or esophageal cancer.

In performing the above methods, the dual EGFR and ErbB-2 inhibitor includes but is not limited to lapatinib or a chemical equivalent thereof. Examples of chemical equivalents are provided above. Additional therapies such as antibody therapies, may be combined with the dual therapy although in one aspect, only the dual therapy or equivalents thereof are to be administered. Further adjuvant therapy such as radiation therapy may be administered where appropriate.

Samples for the screen of the polymorphisms include tumor cells or tissue, normal tissue adjacent to the tumor or normal tissue distal to the tumor, such as peripheral blood lymphocytes. When expression level is tested or screened, the sample should contain or comprise tumor cells or tissue.

Methods to identify the polymorphisms and gene expression levels identified in Tables 1 and 2 above are known in the art and specific examples are provided in the experimental methods. For example, the IL-8 T251A polymorphism is described in Zhang et al. (2005) Clin. Colorectal Cancer 5:124-134. CCD1 (CyclinD1) polymorphism (A870G) is identified by known methods such as those disclosed in Zhang et al. (2006) J. Clin. Oncol. 22(145):3518. EGFR496 is identified by known methods such as those described in Baselga (2005) Nature Clinical Practice Oncology 2:284-285. Methods for identification of the Cox-2 genotype G765C is described in Pereira et al. (2006) World J. Gastroenterol 12:5473-5478 and EGF genotype A61G is described in Goto et al. (2005) Cancer Epidemiol. Biomarkers Prey. 14:2454-2456. HER2 polymorphism A655G was described by Soung et al. (2006) Int. J. Cancer 118:1426-1429. Applicant also previously described suitable methods in U.S. Patent Publ. Nos. 2006/0115827 and 2006/0094012.

Diagnostic Methods

The invention further provides diagnostic methods, which are based, at least in part, on determination of the identity of the polymorphic region or expression level (or both in combination) of the polymorphism identified in Table 1 and/or 2, above.

For example, information obtained using the diagnostic assays described herein is useful for determining if a subject will respond to cancer treatment of a given type. Based on the prognostic information, a doctor can recommend a therapeutic protocol, useful for treating reducing the malignant mass or tumor in the patient or treat cancer in the individual.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Detection of point mutations or additional base pair repeats (as required for the UGT1A1 polymorphism) can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert (Maxam and Gilbert (1997) Proc. Natl Acad Sci. USA 74:560) or Sanger (Sanger et al. (1977) Proc. Nat. Acad. Sci. 74:5463). It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO94/16101, entitled DNA Sequencing by Mass Spectrometry by H. Koster; U.S. Pat. No. 5,547,835 and international patent application Publication Number WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl Biochem Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249; Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility is used to identify the particular allelic variant. For example, single strand conformation polymorphism (SSCP) may be used to detect differences in electrophoretic mobility between mutant and wild type nucleic acids (Orita et al. (1989) Proc Natl. Acad. Sci. USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230 and Wallace et al. (1979) Nucl. Acids Res. 6:3543). Such allele specific oligonucleotide hybridization techniques may be used for the detection of the nucleotide changes in the polymorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell. Probes 6:1).

In another embodiment, identification of the allelic variant is carried out using an oligonucleotide ligation assay (OLA), as described, e.g., in U.S. Pat. No. 4,998,617 and in Landegren, U. et al. Science 241:1077-1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. (1996) Nucleic Acids Res. 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen, D. et al. (French Patent 2,650, 840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al. (1989) Nucl. Acids. Res. 17:7779-7784; Sokolov, B. P. (1990) Nucl. Acids Res. 18:3671; Syvanen, A.-C. et al. (1990) Genomics 8:684-692; Kuppuswamy, M. N. et al. (1991) Proc. Natl. Acad. Sci. (U.S.A.) 88:1143-1147; Prezant, T. R. et al. (1992) Hum. Mutat. 1:159-164; Ugozzoli, L. et al. (1992) GATA 9:107-112; Nyren, P. et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

When antibodies are used, for example when determining the expression level of a marker, antibodies directed against wild type or mutant peptides encoded by the allelic variants of the gene of interest may also be used in disease diagnostics and prognostics. Such diagnostic methods, may be used to detect abnormalities in the level of expression of the peptide, or abnormalities in the structure and/or tissue, cellular, or subcellular location of the peptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al., (1989) supra, at Chapter 18. The protein detection and isolation methods employed herein can also be such as those described in Harlow and Lane, (1988) supra. This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of the peptides or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing disease such as colorectal cancer.

Sample nucleic acid for use in the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo, G. J. (1992) PCR IN SITU HYBRIDIZATION: PROTOCOLS AND APPLICATIONS, Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi, S. and Kramer, F. R. (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis, L. G. (1998) Science 279:1228-9) as has the use of multiple beacons simultaneously (Marras, S. A. (1999) Genet. Anal. 14:151-6). A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88:7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the polymorphism.

Probes and primers can be affixed to supports or surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley, S. O. et al. (1999) Nucleic Acids Res. 27:4830-4837.

Various "gene chips" or "microarray" and similar technologies are know in the art. Examples of such include, but are not limited to LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarraying system that can dispense from 12 to 64 spots onto multiple glass slides (Intelligent Bio-Instruments); Molecular Biology Workstation and NanoChip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "Gene chips" or a "microarray" are also described in US Patent Publ. Nos.: 2007-0111322, 2007-0099198, 2007-0084997, 2007-0059769 and 2007-0059765 and U.S. Pat. Nos. 7,138,506, 7,070,740, and 6,989,267.

In one aspect, "gene chips" or "microarrays" containing probes or primers for genes of Table 1 and/or Table 2, are provided alone or in combination are prepared. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers may be detectably labeled thereby identifying the polymorphism in the gene(s) of interest. Alternatively, a chemical or biological reaction may be used to identify the probes or primers which hybridized with the DNA or RNA of the gene(s) of interest. The genotypes of the patient is then determined with the aid of the aforementioned apparatus and methods.

Nucleic Acids

In one aspect, the nucleic acid sequences of the gene's allelic variants identified in Table 1 and/or 2 above, or portions of said gene, can be the basis for probes or primers, e.g., in methods for determining the identity of the allelic variant of the genes identified in Tables 1 and/or 2. Thus, they can be used in the methods of the invention to determine which therapy is most likely to treat an individual's cancer.

The methods of the invention can use nucleic acids isolated from vertebrates. In one aspect, the vertebrate nucleic acids are mammalian nucleic acids. In a further aspect, the nucleic acids used in the methods of the invention are human nucleic acids.

Primers for use in the methods of the invention are nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the gene of interest, and which by hybridization or absence of hybridization to the DNA of a subject will be indicative of the identity of the allelic variant of the polymorphic region of the gene of interest.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the gene of interest. Thus, such primers can be specific for the gene of interest sequence, so long as they have a nucleotide sequence which is capable of hybridizing to the gene of interest.

The probe or primer may further comprises a label attached thereto, which, e.g., is capable of being detected, e.g. the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane. See, e.g., Letsinger et al., (1989) Proc. Natl. Acad. Sci. U.S.A. 86:6553-6556; Lemaitre et al., (1987) Proc. Natl. Acad. Sci. 84:648-652; and PCT Publication No. WO 88/09810, published Dec. 15, 1988), hybridization-triggered cleavage agents, (see, e.g., Krol et al., (1988) BioTechniques 6:958-976) or intercalating agents (see, e.g., Zon (1988) Pharm. Res. 5:539-549. To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the invention can be prepared according to methods known in the art and described, e.g., in Sambrook et al. (1989) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

Methods of Treatment

The invention further provides methods of treating subjects having solid malignant tissue mass, metastatic or non-metastatic gastrointestinal or breast cancer, such as, for example, rectal cancer, colorectal cancer, (including metastatic CRC), colon cancer, gastric cancer, lung cancer (including non-small cell lung cancer), metastatic breast cancer and inflammatory breast cancer and esophageal cancer. In one embodiment, the method comprises (a) determining the identity of the allelic variant as identified herein; and (b) administering to the subject an effective amount of a compound or therapy (e.g., lapatinib or an equivalent thereof). This therapy can be combined with other suitable therapies or treatments but in one aspect, only the lapatinib or its equivalent is administered.

This invention provides a method for treating a human cancer patient suffering from a gastrointestinal cancer or a breast cancer by administering a composition comprising, or alternatively consisting essentially of, or yet further consisting of, an effective amount of a dual EGFR and ErbB-2 inhibitor to a patient selected for said therapy based on possession of a genetic marker selected from: A/A for IL-8 T251A SNP; low IL-8 expression; or high HER2 expression, thereby treating the patient.

This invention also provides a method for treating a human cancer patient suffering from a gastrointestinal cancer or a breast cancer, comprising administering a composition comprising, or alternatively consisting essentially of, or yet further consisting of, an effective amount of a dual EGFR and ErbB-2 inhibitor to a patient selected for said therapy based on possession of the genetic marker of (T/T or T/C) for VEGF C936T SNP, thereby treating the patient.

The dual EGFR and ErbB-2 inhibitor, such as lapatinib or its chemical or biological equivalent and compositions containing one or more of the same are administered or delivered in an amount effective to treat the cancer and by any suitable means and with any suitable formulation as a composition and therefore includes a carrier such as a pharmaceutically acceptable carrier. Accordingly, a formulation comprising the compounds, compositions, an antibody or biological equivalent thereof is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

When an antibody is administered, the antibodies or biological equivalents thereof can be administered as a composition. Chemical compounds also can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

The antibody or equivalent thereof is prepared to a concentration includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

The compositions and formulations of the present invention can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject®' NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provisio that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

An "effective amount" is an amount sufficient to effect beneficial or desired results. An effective amount can be administered in one or more administrations, applications or dosages.

The invention provides an article of manufacture, comprising packaging material and at least one vial comprising a solution of a compound or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising the compound and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The lapatinib or equivalent thereof is prepared to a concentration includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

The formulations of the present invention can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a chemotherapeutic and/or a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject®' NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a therapeutic agent of the invention, e.g., encapsulation in liposomes, microparticles, microcapsules, expression by recombinant cells, receptor-mediated endocytosis. See e.g., Wu and Wu (1987) J. Biol. Chem. 262:4429-4432, for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the invention locally to the area in need of treatment; this may be achieved by, for example, and not by way of limitation, local infusion during surgery, by injection or by means of a catheter.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Also provided is a medicament comprising an effective amount of a chemotherapeutic or a chemical equivalent or biological equivalent thereof, as described herein for treatment of a human cancer patient having one or more predictive polymorphisms or genetic markers as identified in Table 1 or the experimental examples.

Biological Equivalent Antibodies and Therapies

In one aspect, after determining that antibody therapy alone or in combination with other suitable therapy is likely to provide a benefit to the patient, the invention further comprises administration of the chemotherapy as described herein, alone or in combination with anti-angiogenic antibody, fragment, variant or derivative thereof. The antibodies of this invention are monoclonal antibodies, although in certain aspects, polyclonal antibodies can be utilized. They also can be functional fragments, antibody derivatives or antibody variants. They can be chimeric, humanized, or totally human. A functional fragment of an antibody includes but is not limited to Fab, Fab', Fab2, Fab'2, and single chain variable regions. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding or neutralization ability as the antibodies of this invention it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

When an antibody is used as a therapeutic or diagnostic tool, the proposed antibodies or their equivalents can be used. Equivalent antibodies can be characterized by their ability to specifically bind to an equivalent epitope. The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994).

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody variant" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured there from. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Russel, N. D. et al. (2000) Infection and Immunity April: 1820-1826; Gallo, M. L. et al. (2000) European J. of Immun. 30:534-540; Green, L. L. (1999) J. of Immun. Methods 231: 11-23; Yang, X-D et al. (1999A) J. of Leukocyte Biology 66:401-410; Yang, X-D (1999B) Cancer Research 59(6): 1236-1243; Jakobovits, A. (1998) Advanced Drug Delivery Reviews 31:33-42; Green, L. and Jakobovits, A. (1998) J. Exp. Med. 188(3):483-495; Jakobovits, A. (1998) Exp. Opin. Invest. Drugs 7(4):607-614; Tsuda, H. et al. (1997) Genomics 42:413-421; Sherman-Gold, R. (1997) Genetic Engineering News 17(14); Mendez, M. et al. (1997) Nature Genetics 15:146-156; Jakobovits, A. (1996) WEIR'S HANDBOOK OF EXPERIMENTAL IMMUNOLOGY, THE INTEGRATED IMMUNE SYSTEM Vol. IV, 194.1-194.7; Jakobovits, A. (1995) Current Opinion in Biotechnology 6:561-566; Mendez, M. et al. (1995) Genomics 26:294-307; Jakobovits, A. (1994) Current Biology 4(8):761-763; Arbones, M. et al. (1994) Immunity 1(4):247-260; Jakobovits, A. (1993) Nature 362(6417):255-258; Jakobovits, A. et al. (1993) Proc. Natl. Acad. Sci. USA 90(6):2551-2555; Kucherlapati, et al. U.S. Pat. No. 6,075,181.

Human monoclonal antibodies can also be produced by a hybridoma which includes a B cell obtained from a transgenic nonhuman animal, e.g., a transgenic mouse, having a genome comprising a human heavy chain transgene and a light chain transgene fused to an immortalized cell.

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

The term "antibody derivative" also includes "diabodies" which are small antibody fragments with two antigen-binding sites, wherein fragments comprise a heavy chain variable domain (V) connected to a light chain variable domain (V) in the same polypeptide chain (VH V). See for example, EP 404,097; WO 93/11161; and Hollinger et al. (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.

The term "antibody derivative" further includes "linear antibodies". The procedure for making the is known in the art and described in Zapata et al. (1995) Protein Eng. 8(10): 1057-1062. Briefly, these antibodies comprise a pair of tandem Fd segments (V-C1-VH-C1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The anti-angeogenic antibody can be further modified. The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis. See generally, Hermanson, G. T., BIOCONJUGATE TECHNIQUES, Biological Equivalent Antibodies and Therapies In one aspect, after determining that antibody therapy alone or in combination with other suitable therapy is likely to provide a benefit to the patient, the invention further comprises administration of an anti-angiogenic antibody, fragment, variant or derivative thereof. The antibodies of this invention are monoclonal antibodies, although in certain aspects, polyclonal antibodies can be utilized. They also can be functional fragments, antibody derivatives or antibody variants. They can be chimeric, humanized, or totally human. A functional fragment of an antibody includes but is not limited to Fab, Fab', Fab2, Fab'2, and single chain variable regions. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding or neutralization ability as the antibodies of this invention it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

The antibodies also are characterized by their ability to specifically bind to an equivalent epitope. The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994).

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody variant" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured there from. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Russel, N. D. et al. (2000) Infection and Immunity April: 1820-1826; Gallo, M. L. et al. (2000) European J. of Immun. 30:534-540; Green, L. L. (1999) J. of Immun. Methods 231: 11-23; Yang, X-D et al. (1999A) J. of Leukocyte Biology 66:401-410; Yang, X-D (1999B) Cancer Research 59(6): 1236-1243; Jakobovits, A. (1998) Advanced Drug Delivery Reviews 31:33-42; Green, L. and Jakobovits, A. (1998) J. Exp. Med. 188(3):483-495; Jakobovits, A. (1998) Exp. Opin. Invest. Drugs 7(4):607-614; Tsuda, H. et al. (1997) Genomics 42:413-421; Sherman-Gold, R. (1997) Genetic Engineering News 17(14); Mendez, M. et al. (1997) Nature Genetics 15:146-156; Jakobovits, A. (1996) WEIR'S HANDBOOK OF EXPERIMENTAL IMMUNOLOGY, THE INTEGRATED IMMUNE SYSTEM Vol. IV, 194.1-194.7; Jakobovits, A. (1995) Current Opinion in Biotechnology 6:561-566; Mendez, M. et al. (1995) Genomics 26:294-307; Jakobovits, A. (1994) Current Biology 4(8):761-763; Arbones, M. et al. (1994) Immunity 1(4):247-260; Jakobovits, A. (1993) Nature 362(6417):255-258; Jakobovits, A. et al. (1993) Proc. Natl. Acad. Sci. USA 90(6):2551-2555; Kucherlapati, et al. U.S. Pat. No. 6,075,181.

Human monoclonal antibodies can also be produced by a hybridoma which includes a B cell obtained from a transgenic nonhuman animal, e.g., a transgenic mouse, having a genome comprising a human heavy chain transgene and a light chain transgene fused to an immortalized cell.

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

The term "antibody derivative" also includes "diabodies" which are small antibody fragments with two antigen-binding sites, wherein fragments comprise a heavy chain variable domain (V) connected to a light chain variable domain (V) in the same polypeptide chain (VH V). See for example, EP 404,097; WO 93/11161; and Hollinger et al. (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.

The term "antibody derivative" further includes "linear antibodies". The procedure for making the is known in the art and described in Zapata et al. (1995) Protein Eng. 8(10): 1057-1062. Briefly, these antibodies comprise a pair of tandem Fd segments (V-C1-VH-C1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The anti-angiogenic antibody can be further modified. The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis. See generally, Hermanson, G. T. (1996) BIOCONJUGATE TECHNIQUES, Academic Press: San Diego, Calif.

Kits

As set forth herein, the invention provides diagnostic methods for determining the type of allelic variant of a polymorphic region present in the gene of interest or the expression level of a gene of interest. In some embodiments, the methods use probes or primers comprising nucleotide sequences which are complementary to the polymorphic region of the gene of interest or that are useful to identify the expression level of the gene of interest. Accordingly, the invention provides kits for performing these methods as well as instructions for carrying out the methods of this invention such as collecting tissue and/or performing the screen, and/or analyzing the results, and/or administration of an effective amount of the dual therapies described herein, alone or in combination with other suitable chemotherapy or biological therapy.

In an embodiment, the invention provides a kit for determining whether a subject responds to cancer treatment or alternatively one of various treatment options. The kits contain one of more of the compositions described above and instructions for use. As an example only, the invention also provides kits for determining response to cancer treatment containing a first and a second oligonucleotide specific for the polymorphic region of the gene. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide. Polynucleotides or other agents, such as antibodies, can be further included to determine the expression level of IL-8 and/or HER-2.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard, T. (1986) AN INTRODUCTION TO RADIOIMMUNOASSAY AND RELATED TECHNIQUES Elsevier Science Publishers, Amsterdam, The Netherlands; Bullock, G. R. et al., TECHNIQUES IN IMMUNOCYTOCHEMISTRY Academic Press, Orlando, Fla. Vol. 1 (1982), Vol. 2 (1983), Vol. 3 (1985); Tijssen, P. (1985) PRACTICE AND THEORY OF IMMUNOASSAYS: LABORATORY TECHNIQUES IN BIOCHEMISTRY AND MOLECULAR BIOLOGY, Elsevier Science Publishers, Amsterdam, The Netherlands.

The test samples used in the diagnostic kits include cells, tissue, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the gene of interest.

As amenable, these suggested kit components may be packaged in a manner customary for use by those of skill in the art. For example, these suggested kit components may be provided in solution or as a liquid dispersion or the like.

Other Uses for the Nucleic Acids of the Invention

The identification of the allele of the gene of interest can also be useful for identifying an individual among other individuals from the same species. For example, DNA sequences can be used as a fingerprint for detection of different individuals within the same species. Thompson, J. S, and Thompson, eds., (1991) "Genetics in Medicine", W B Saunders Co., Philadelphia, Pa. This is useful, e.g., in forensic studies.

The invention now being generally described, it will be more readily understood by reference to the following examples which are included merely for purposes of illustration of certain aspects and embodiments of the present invention, and are not intended to limit the invention.

EXPERIMENTAL EXAMPLES

Experiment No. 1

For the purpose of illustration only, peripheral blood sample can be collected from each patient, and genomic DNA can be extracted from white blood cells using the QiaAmp kit (Qiagen, Valencia, Calif.).

Background Lapatinib (GW572016) is a dual tyrosine kinase inhibitor of EGFR and HER2. In SWOG 0413 trial, advanced or metastatic gastric cancer patients were treated with lapatinib. This study investigated whether gene expressions and polymorphisms of EGFR and angiogenesis pathway genes were associated with clinical outcome in the patients enrolled in SWOG 0413 trial.

Methods A total of 46 patients were enrolled in SWOG 0413 trial and treated with lapatinib. Blood and tissue samples were available from 40 and 37 patients, respectively. RT-PCR was performed for intratumoral gene expression levels of EGFR, HER2, VEGF, IL-8, COX2 and Cyclin D1 genes. Eight polymorphisms in the EGF, EGFR, HER2, VEGF, IL-8, COX2 and cyclin D1 genes were also analyzed by PCR-RFLP.

Results Patients who have lower IL-8 [median overall survival (OS), 6 vs 3 months, p=0.03] and higher HER2 (6 vs 3 months, p=0.005) gene expression levels showed better overall survival. According to gene polymorphisms, patients who have A/A genotype of IL-8 T251A polymorphism showed a trend for improved overall survival over those with the other 2 genotypes (median OS, 10 vs 3 vs 3 months, p=0.07).

Conclusion These results show that intratumoral gene expression levels of HER2 and IL-8 are potential molecular predictors for survival in patients with advanced or metastatic gastric cancer treated with lapatinib.

Experiment No. 2

Background Lapatinib (GW572016) is a dual tyrosine kinase inhibitor of EGFR and HER2. In SWOG0413 trial, advanced or metastatic gastric cancer patients were treated with lapatinib. In this study, whether gene expressions and polymorphisms of EGF and angiogenesis pathway genes were associated with clinical outcome in the patients enrolled in SWOG0413 trial were investigated.

Methods A total of 46 patients were enrolled in SWOG0413 trial and treated with lapatinib. Blood and tissue samples were available from 42 and 37 patients, respectively. RT-PCR was performed for intratumoral gene expression levels of EGFR, HER2, VEGF, IL-8, COX2 and cyclin D1 genes. 8 polymorphisms in the EGF, EGFR, HER2, VEGF, IL-8, COX2 and cyclin D1 genes by PCR-RFLP were tested. Probes/primers for these analysis are known in the art and examples are provided in Table 3 and 4, below.

Results Patients who have lower IL-8 [median overall survival (OS), 6 vs 3 months, p=0.03] and higher HER2 (6 vs 3 months, p=0.005) gene expression levels showed better OS. According to gene polymorphisms, patients who have A allele of IL-8 T251A polymorphism showed improved OS (A/A, 10 months vs T/A, 5 months vs T/T 3 months, p=0.04). And patients with A allele of IL-8 T251A and T allele of VEGF C936T polymorphisms showed better response rates (p<0.01, p<0.01, respectively). All other polymorphisms and gene expressions did not show significant association with clinical outcome.

Conclusions These results suggest that intratumoral gene expression levels of HER2 and IL-8 and polymorphism in IL-8 are potential molecular predictors for survival in patients with advanced or metastatic gastric cancer treated with lapatinib. And polymorphisms in IL-8 and VEGF genes may be potential markers in predicting response in this population. A larger prospective study is needed to validate and confirm these preliminary findings.

TABLE 3

Probe and Primer Sequences for Determining Gene Expression Levels

| Gene | Forward Primer (5'-3') | Reverse Primer (5'-3') | Taqman Probe (5'-3') |
|---|---|---|---|
| Beta-actin | GAGCGCGGCTACAGCTT (SEQ ID NO: 1) | TCCTTAATGTCACGCACG ATTT (SEQ ID NO: 2) | ACCACCACGGCCGAG CGG (SEQ ID NO: 3) |
| IL-8 | CAGCTCTGTGTGAAGGT GCAGTT (SEQ ID NO: 4) | GGGTGGAAAGGTTTGGA GTATGTC (SEQ ID NO: 5) | TGCACTGACATCTAAG TTCTTTAGCACTCCTT GGC (SEQ ID NO: 6) |
| HER2 | AGA GCG CCA GCC CTC TGA CGT CCA T (SEQ ID NO: 7) | TCC GTT TCC TGC AGC AGT CTC CGC A (SEQ ID NO: 8) | Not applicable. |
| EGFR | TGCGTCTCTTGCCGGAA T (SEQ ID NO: 9) | GGCTCACCCTCCAGAAGC TT (SEQ ID NO: 10) | ACGCATTCCCTGCCTC GGCTG (SEQ ID NO: 11) |
| VEGF | AGTGGTCCCAGGCTGCA C (SEQ ID NO: 12) | TCCATGAACTTCACCACT TCGT (SEQ ID NO: 13) | ATGGCAGAAGGAGGA GGGCAGAATCA (SEQ ID NO: 14) |
| COX-2 | GCTCAACATGATGTTTG CATTC (SEQ ID NO: 15) | GCTGGCCCTCGCTTATGA (SEQ ID NO: 16) | TGCCCAGCACTTCACG CATCAGTT (SEQ ID NO: 17) |
| Cyclin D1 | TGCATGTTCGTGGCCTCT AA (SEQ ID NO: 18) | TCGGTGTAGATGCACAGC TTCT (SEQ ID NO: 19) | AAGGAGACCATCCCCC TGACGGC (SEQ ID NO: 20) |

TABLE 4

Primer Sequences, Annealing Temperatures and Restriction Enzymes for Determining Polymorphisms

| Gene | Forward-Primer (5'-3') | Reverse-Primer (5'-3') | Enzyme | Annealing |
|---|---|---|---|---|
| VEGF C + 936T | AAGGAAGAGGAGAC T CTGCGCAGAGC (SEQ ID NO: 21) | TAAATGTATGTATGTGGG TGGGTGTGTCTACAGG (SEQ ID NO: 22) | Nla III | 60° |
| IL8 T − 251A | TTGTTCTAACACCTG CCACTCT (SEQ ID NO: 23) | GGCAAACCTGAGTC TCACA (SEQ ID NO: 24) | Mfe I | 60° |
| EGF A61G | CATTTGCAAACAGAG GCTCA (SEQ ID NO: 25) | TGTGACAGAGCAAGGCAA AG (SEQ ID NO: 26) | Alu I | 60° |
| EGFR G497A | TGCTGTGACCCACTC TGTCT (SEQ ID NO: 27) | CCAGAAGGTTGCACTTGT CC (SEQ ID NO: 28) | Bst-NI | 59° |
| HER2 A655G | AGA GCG CCA GCC CTC TGA CGT CCA T (SEQ ID NO: 29) | TCC GTT TCC TGC AGC AGT CTC CGC A (SEQ ID NO: 30) | BsmAI | 55° |
| COX-2 G765C | CCGCTTCCTTTGTCCA TCAG (SEQ ID NO: 31) | GGCTGTATATCTGCTCTAT ATGC (SEQ ID NO: 32) | Aci I | 55° |
| Cyclin D1 A870G | GTGAAGTTCATTTCC AATCCGC (SEQ ID NO: 33) | GGACATCACCCTCACTTAC (SEQ ID NO: 34) | ScrF I | 55° |

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for treating a human cancer patient suffering from gastric cancer, comprising administering an effective amount of lapatinib to a gastric cancer patient selected for said therapy based on possession of a genetic marker A/A for IL-8 T251A SNP, thereby treating said patient.

2. The method of claim 1, wherein the patient is suffering from advanced or metastatic gastric cancer.

3. The method of claim 1, further comprising administering an effective amount of a therapy selected from trastuzumab, capecitabine, letrozole, paclitaxel and FOLFIRI (irinotecan, 5-fluorouracil and leucovorin).

4. The method of claim 1, wherein the (A/A) for IL-8 T251A SNP is determined by Polymerase Chain Reaction-Restriction Fragment Length Polymorphism (PCR-RFLP) of a tissue sample isolated from the patient.

5. The method of claim 1, wherein gene expression of IL-8 is determined by Reverse Transcriptase-Polymorphism Cain Reaction (RT-PCR).

6. The method of claim 1, wherein the patient is selected for the therapy aided by the determination that the patient is more likely responsive to the therapy than a patient lacking possession of the A/A for IL-8 T251A SNP genetic marker or more likely to experience longer overall survival than a patient lacking possession of the A/A for IL-8 T251A SNP genetic marker.

* * * * *

SEQUENCE LISTING

<160> NUMBER OF SEQ ID NOS: 34

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagcgcggct acagctt                                                   17

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccttaatgt cacgcacgat tt                                             22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
accaccacgg ccgagcgg                                                  18

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagctctgtg tgaaggtgca gtt                                            23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggtggaaag gtttggagta tgtc                                           24

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6

```
tgcactgaca tctaagttct ttagcactcc ttggc                                  35

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agagcgccag ccctctgacg tccat                                             25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccgtttcct gcagcagtct ccgca                                             25

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgcgtctctt gccggaat                                                     18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggctcaccct ccagaagctt                                                   20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
acgcattccc tgcctcggct g                                                 21

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtggtccca ggctgcac                                                     18
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tccatgaact tcaccacttc gt                                          22

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
atggcagaag gaggagggca gaatca                                      26

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctcaacatg atgtttgcat tc                                          22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctggccctc gcttatga                                               18

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tgcccagcac ttcacgcatc agtt                                        24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgcatgttcg tggcctctaa                                             20

<210> SEQ ID NO 19

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcggtgtaga tgcacagctt ct                                              22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aaggagacca tccccctgac ggc                                             23

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaggaagagg agactctgcg cagagc                                          26

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
taaatgtatg tatgtgggtg ggtgtgtcta cagg                                 34

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttgttctaac acctgccact ct                                              22

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcaaacctg agtctcaca                                                  19

<210> SEQ ID NO 25
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
catttgcaaa cagaggctca                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgtgacagag caaggcaaag                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgctgtgacc cactctgtct                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccagaaggtt gcacttgtcc                                              20

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agagcgccag ccctctgacg tccat                                        25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tccgtttcct gcagcagtct ccgca                                        25

<210> SEQ ID NO 31
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 31
ccgcttcctt tgtccatcag                                              20

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggctgtatat ctgctctata tgc                                          23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgaagttca tttccaatcc gc                                           22

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggacatcacc ctcacttac                                               19
```